(12) United States Patent
Chappo et al.

(10) Patent No.: US 11,348,964 B2
(45) Date of Patent: May 31, 2022

(54) PIXEL DEFINITION IN A POROUS SILICON QUANTUM DOT RADIATION DETECTOR

(71) Applicants: KONINKLIJKE PHILIPS N.V., Eindhoven (NL); WAYNE STATE UNIVERSITY, Detroit, MI (US)

(72) Inventors: Marc Anthony Chappo, Elyria, OH (US); Stephanie Lee Brock, Ferndale, MI (US)

(73) Assignees: KONINKLIJKE PHILIPS N.V., Eindhoven (NL); WAYNE STATE UNIVERSITY, Detroit, MI (US)

( * ) Notice: Subject to any disclaimer, the term of this patent is extended or adjusted under 35 U.S.C. 154(b) by 49 days.

(21) Appl. No.: 17/041,745

(22) PCT Filed: Mar. 28, 2019

(86) PCT No.: PCT/EP2019/057921
§ 371 (c)(1),
(2) Date: Sep. 25, 2020

(87) PCT Pub. No.: WO2019/185831
PCT Pub. Date: Oct. 3, 2019

(65) Prior Publication Data
US 2021/0126037 A1    Apr. 29, 2021

Related U.S. Application Data

(60) Provisional application No. 62/649,615, filed on Mar. 29, 2018.

(51) Int. Cl.
| | |
|---|---|
| *G01T 1/16* | (2006.01) |
| *H01L 27/146* | (2006.01) |
| *G01T 1/24* | (2006.01) |
| *H01L 31/028* | (2006.01) |

(Continued)

(52) U.S. Cl.
CPC ........ *H01L 27/14659* (2013.01); *A61B 6/032* (2013.01); *G01T 1/1603* (2013.01);
(Continued)

(58) Field of Classification Search
CPC .............................. A61B 6/032; G01T 1/1603
See application file for complete search history.

(56) References Cited

U.S. PATENT DOCUMENTS

| | | |
|---|---|---|
| 8,581,254 B2 | 11/2013 | Couture |
| 2012/0175584 A1 | 7/2012 | Weinberg |

(Continued)

FOREIGN PATENT DOCUMENTS

| | | |
|---|---|---|
| KR | 20070040124 A | 4/2007 |
| WO | WO2017025888 A1 | 2/2017 |

(Continued)

OTHER PUBLICATIONS

Urdaneta et al. Porous silicon-based quantum dot broad spectrum radiation detector Journal of Instrumentation vol. 6 C01027, 6 pages (Year: 2011).*

(Continued)

*Primary Examiner* — David P Porta
*Assistant Examiner* — Shun Lee
(74) *Attorney, Agent, or Firm* — Larry Liberchuk

(57) ABSTRACT

An imaging module (114) of an imaging system comprises a porous silicon membrane (116) with a first side (208), a contact side (210) opposite the first side, columns of silicon (212) configured to extend from the first side to the contact side, and columnar holes (214, 502) interlaced with the columns of silicon and configured to extend from the first side to the contact side. The imaging module further includes quantum dots (118) in the columnar holes. The imaging module further includes a metal pad (120) electrically coupled to the columns of silicon of the porous silicon membrane. The quantum dots in the columnar holes are electrically insulated from the metal pad. The imaging module further includes a substrate (122) with an electrically (Continued)

conductive pad (204) in electrical communication with the metal pad that defines a pixel.

20 Claims, 7 Drawing Sheets

(51) Int. Cl.
*H01L 31/0352* (2006.01)
*A61B 6/03* (2006.01)
(52) U.S. Cl.
CPC .......... *G01T 1/241* (2013.01); *H01L 31/0284* (2013.01); *H01L 31/035218* (2013.01)

(56) References Cited

U.S. PATENT DOCUMENTS

| | | |
|---|---|---|
| 2015/0331115 A1 | 11/2015 | Nelson |
| 2016/0084476 A1 | 3/2016 | Koole |
| 2017/0306221 A1 | 10/2017 | Koole |

FOREIGN PATENT DOCUMENTS

| | | |
|---|---|---|
| WO | WO2017163149 A1 | 9/2017 |
| WO | WO2017194833 A1 | 11/2017 |
| WO | WO2018077681 A1 | 5/2018 |

OTHER PUBLICATIONS

PCT International Search Report, International application No. PCT/EP2019/057921, dated Jul. 17, 2019.

Urdaneta M et al., "Porous Silicon-Based Quantum Dot Broad Spectrum Radiation Detector", Journal of Instrumentation, Institute of Physics Publishing, Bristol, GB, vol. 6, No. 1, Jul. 11-15, 2010.

Kumari P. N. et al., "QCA System Design Using Blocks with vertically Stacked Active Elements", 2nd International Conference on Devices, Circuits and Systems (ICDCS), pp. 1-6, 2014.

\* cited by examiner

PIXEL DEFINITION IN A POROUS SILICON QUANTUM DOT RADIATION DETECTOR

FIELD OF THE INVENTION

The following generally relates to imaging and more particular to pixel definition in a porous silicon (pSi) quantum dot (QD) radiation detector, and is described with particular application to computed tomography (CT) imaging.

BACKGROUND OF THE INVENTION

Computed tomography radiation detectors are largely comprised of crystal or garnet scintillators directly mounted to solid-state photodetectors such as photodiodes. The scintillator material produces light photons in response to bombardment with X-ray photons, which are then converted to electrical currents or pulses in the photodetector. Dual-energy spectral CT detectors include two scintillators stacked one on top of the other with photodetectors on their sides and are relatively expensive. Planar versions that have photodetectors in between scintillator layers require flex circuitry or a complex interconnect to bypass the intermediate layer(s) of scintillator(s). Spectral CT detectors made of Cadmium Zinc Telluride (CZT) or Cadmium Telluride (CdTe) have been utilized in limited applications, e.g., due to high cost, yield and/or performance issues.

Radiation detectors comprising Quantum Dot (QD) radiation absorptive materials in columns of porous silicon (pSi) membranes (i.e. QD-pSi radiation detectors) improve performance while lowering cost and decreasing thickness. QD-pSi radiation detectors require a connection to predefined areas of the Si without contacting the QD's in the pores (columns) in order to define a pixel area. In commercially available pSi membranes, the columns extend entirely through the pSi membrane and thus the QD's in the columns also extend from one side to the other side of the pSi membrane. As a consequence, while the definition of the pixel can be made by applying an electrically conductive contact having a predetermined size or by contacting an electrically conductive contact on a substrate, such an electrically conductive contact would also electrically contact the QD's in the pores of pSi membranes.

SUMMARY OF THE INVENTION

Aspects described herein address the above-referenced problems and others. In one aspect, an imaging module of an imaging system comprises a porous silicon membrane with a first side, a contact side opposite the first side, columns of silicon configured to extend from the first side to the contact side, and columnar holes interlaced with the columns of silicon and configured to extend from the first side to the contact side. The imaging module further includes quantum dots in the columnar holes. The imaging module further includes a metal pad electrically coupled to the columns of silicon of the porous silicon membrane. The quantum dots in the columnar holes are electrically insulated from the metal pad. The imaging module further includes a substrate with electrically conductive pads in electrical communication with the metal pad.

In another aspect, a computed tomography imaging system includes a radiation source configured to emit X-ray radiation, a detector array configured to detect X-ray radiation and generate an electrical signal indicative thereof, and a reconstructor configured to process the electrical signal and reconstruct volumetric image data. The detector array includes a pixel that comprises a first porous silicon membrane with first columns of silicon and first columnar holes with first quantum dots, a first metal pad electrically coupled to the first columns of silicon and electrically insulated from the first quantum dots, and a reconstructor configured to process the electrical signal and reconstruct volumetric image data.

In another aspect, a method includes obtaining at least one porous silicon membrane having columns of silicon and columnar holes therethrough, filling the columnar holes with quantum dots, creating an insulator on a contact side of the porous silicon membrane for the quantum dots, and electrically coupling only the columns of silicon to a substrate, wherein the quantum dots are electrically insulated from the substrate through the insulator.

Still further aspects of the present invention will be appreciated to those of ordinary skill in the art upon reading and understand the following detailed description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

The following generally describes an imaging system with a QD-pSi radiation detector that includes a pSi membrane with columnar holes that extend entirely through the Si and that are filled with QD's, which are electrically insulated (e.g., via an air gap or insulation material) from a metal pad that defines a size of a pixel. In one instance, this configuration preserves the cost reduction afforded by pSi and retains the performance of simultaneous spectral and spatial resolution inherent in a pSi/QD radiation detector.

Figure 1:
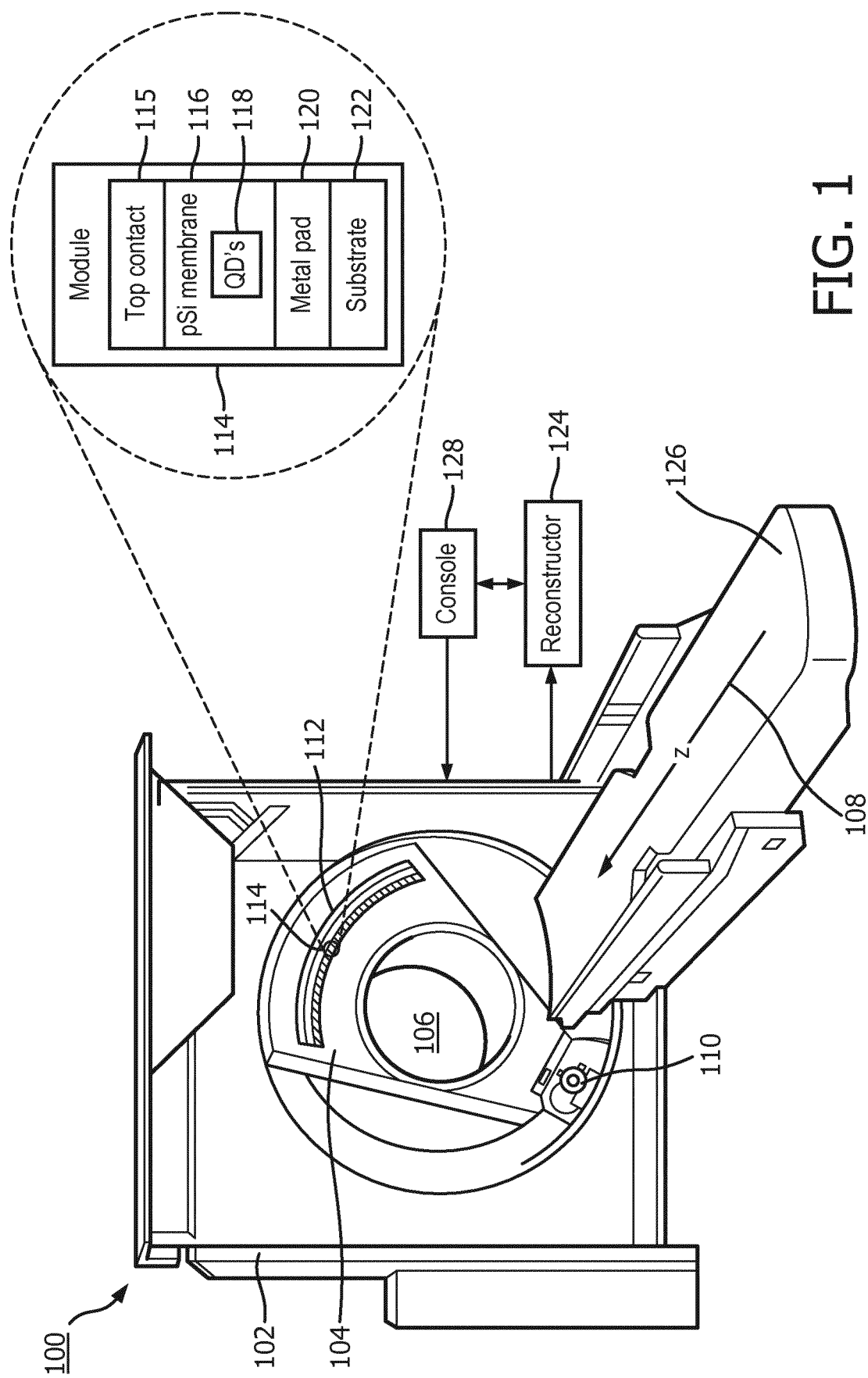
FIG. 1 schematically illustrates an example CT imaging system with a QD-pSi radiation detector.

FIG. 1 schematically illustrates an example imaging system 100 such as a computed tomography (CT) system configured for spectral and/or non-spectral imaging. The imaging system 100 includes a stationary gantry 102 and a rotating gantry 104, which is rotatably supported by the stationary gantry 102. The rotating gantry 104 rotates around an examination region 106 about a longitudinal or z-axis 108. A radiation source 110, such as an x-ray tube, is supported by the rotating gantry 104, rotates therewith, and generates and emits X-ray radiation.

A radiation sensitive detector array 112 includes one or more rows arranged parallel to each other along the z-axis 108 direction, each row including a plurality of detector modules 114 extending transverse to the z-axis 108 direction. The modules 114 detect X-ray radiation traversing the examination region 106 and generate electrical signals (projection data) indicative thereof. At least one of the modules 114 includes a top contact 115, a pSi membrane 116 with columnar holes filled with QD's 118, a metal pad 120, and a substrate 122 electrically coupled to the Si in the pSi membrane 116 via the metal pad 120. A size of a pixel is defined by a size of the metal pad 120, as described in greater detail below.

Also described in greater detail below, in one instance, the columnar holes extend all the way through the pSi membrane 116 and the QD's 118 in the columnar holes are electrically insulated from the metal pad 120. In one instance, this is accomplished by ensuring that the QDs are either recessed relative to a plane of the pSi such that a separate substrate bonded to the to the pSi plane only contacts the pSi columns within a pixel and not the QDs, or with a Si contact layer on the pSi die that only contacts the columns of pSi and not the QD's. For the former, the recess can be empty or filled with an insulating material to prohibit contact with the QDs in the column.

A reconstructor 124 reconstructs the electrical signals with one or more reconstruction algorithms. In one instance, the one or more reconstruction algorithms includes one or more spectral reconstruction algorithms and/or at least one non-spectral reconstruction algorithm. The one or more reconstruction algorithms reconstruct spectral volumetric image data corresponding to one or more different energy spectra, basis component, and/or material composition. The at least one non-spectral reconstruction algorithm reconstructs non-spectral volumetric image data corresponding to a mean energy spectrum of the X-ray beam.

A subject support 126, such as a couch, supports an object or subject in the examination region 106 so as to guide the subject or object with respect to the examination region 106 for loading, scanning, and/or unloading the subject or object. A computing system serves as an operator console 128 and includes a human readable output device such as a display, an input device such as a keyboard, mouse, and/or the like, one or more processors and computer readable storage medium. Software resident on the console 128 allows an operator to control an operation of the imaging system 100.

Figure 2:
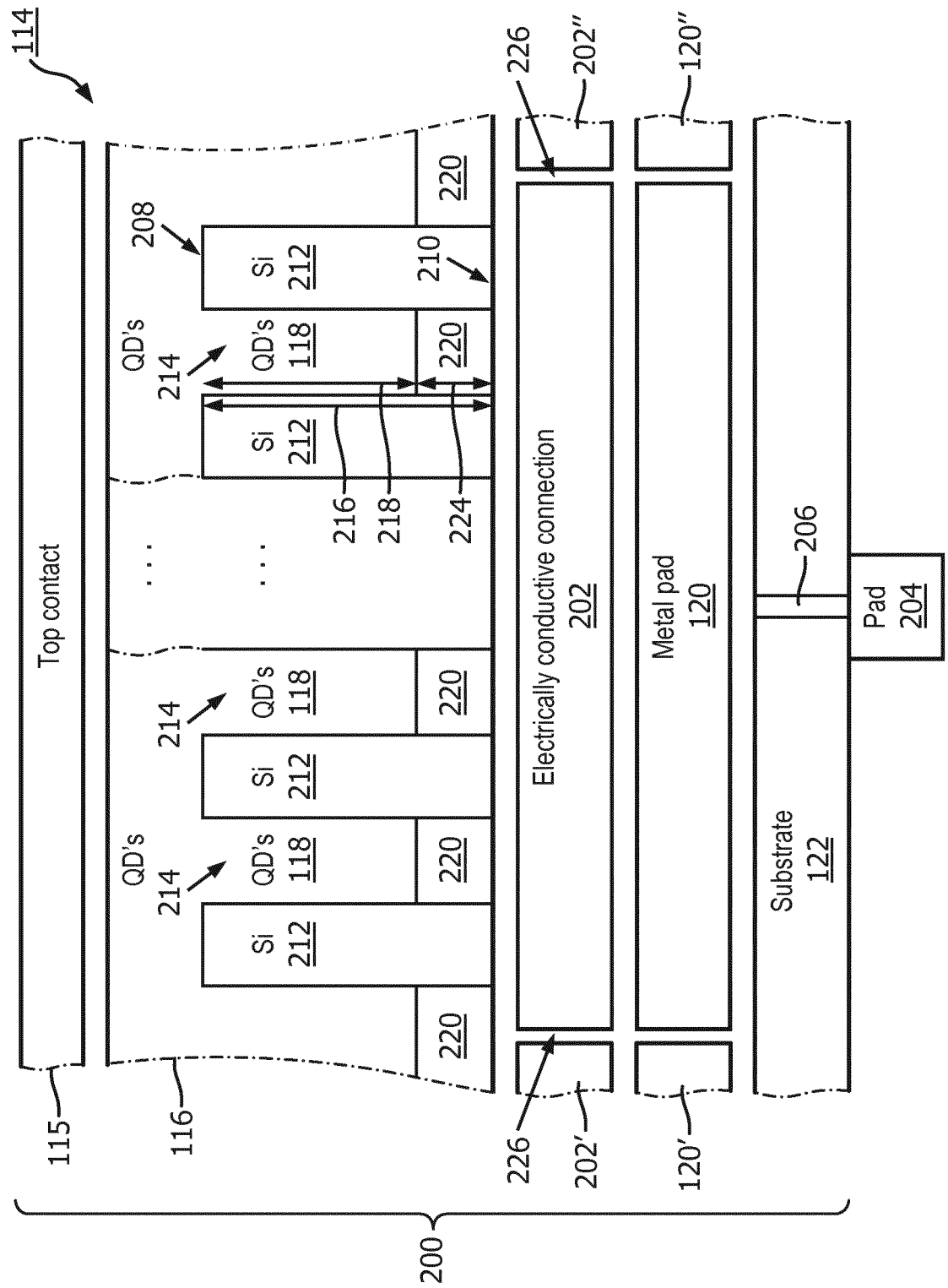
FIG. 2 schematically illustrates an exploded view of an example of a portion of a module of the QD-pSi radiation detector of FIG. 1.
Figure 3:
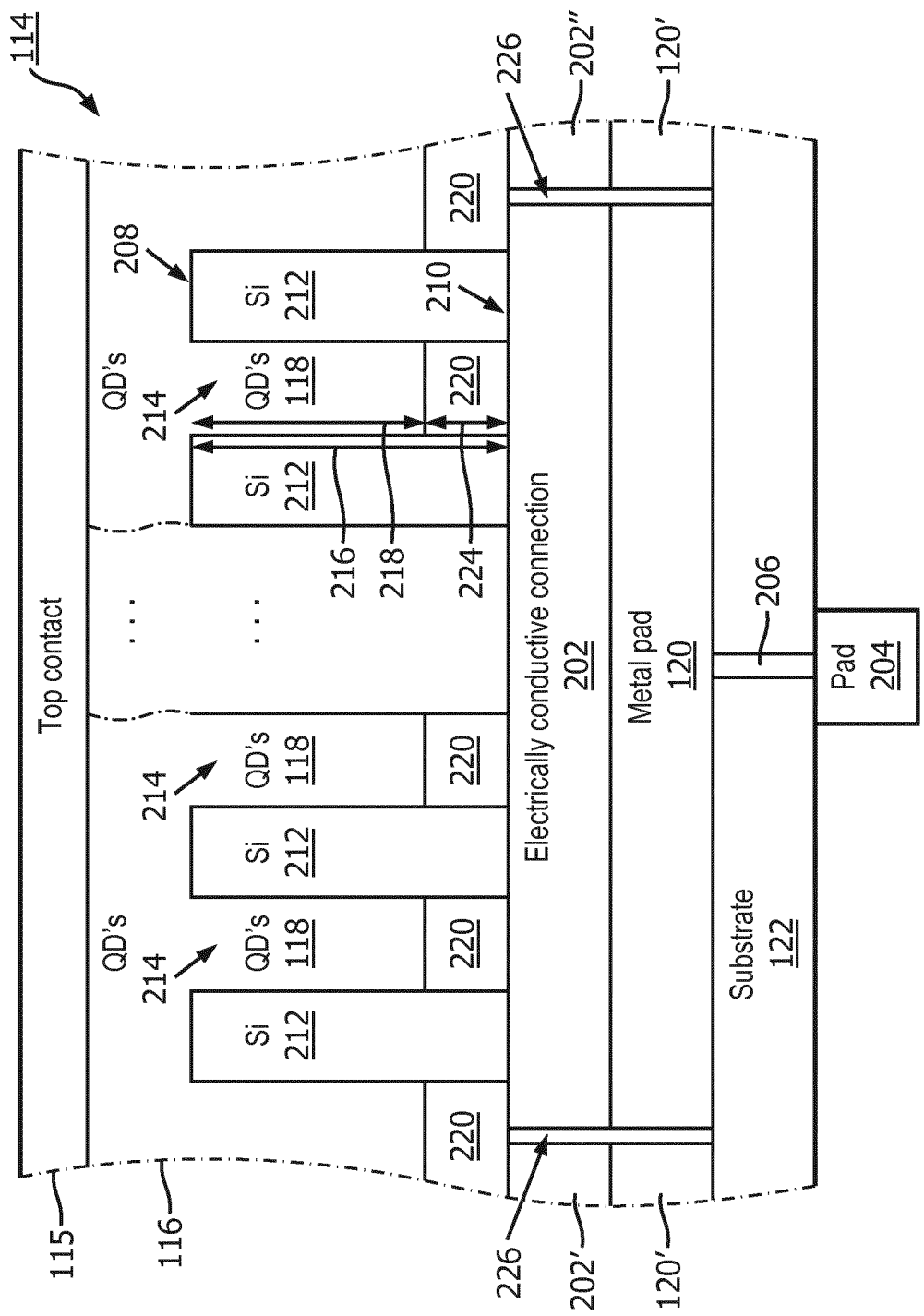
FIG. 3 schematically illustrates the example of the portion of the module of the QD-pSi radiation detector of FIG. 1.

FIGS. 2 and 3 schematically illustrate an example pixel of the module 114. FIG. 2 includes an exploded view 200. The module 114 includes the top contact 115, the pSi membrane 116, an electrically conductive connection 202 (e.g., an electrically conductive adhesive and/or conductive connection), the metal pad 120, and the substrate 122 with one or more electrically conductive pads 204 and one or more electrically conductive vias 206. In one instance, the substrate 122 includes an integrated circuit (IC), an application specific integrated circuit (ASIC), or the like.

In this example, the pSi membrane 116 includes a first side 208 and a second (contact) side 210. The first side 208 is adjacent to the top contact 115 and faces the examination region 106 (FIG. 1) and the second side 210 faces the electrically conductive connection 202. The pSi membrane 116 includes a plurality of columns, including columns of Si 212 interlaced with columnar holes 214. The pSi membrane 116 and hence the columns of Si 212 and the columnar holes 214 have a height 216 (on the order of hundreds of microns) from the first side 208 to the second side 210. The widths of the columns of Si 212 and the columnar holes 214 are on the order of microns.

The columnar holes 214 of the pSi membrane 116 are filled with QD's 118 from the first side 208 to a depth 218, which is less than the height 216. A recess 220 of the columnar holes 214 of the pSi membrane 116 from the QD's 118 to the second side 210 and has a depth 224 (e.g., a smallest practical depth), which also is less than the height 216. In general, a summation of the depths 218 and 224 add up to the height 216. In one instance, the recess 220 is an empty, material free space. In another instance, the recess 220 is filled with an insulating material such as silicon dioxide, etc.

The QD's 118 in the columnar holes 214 and the Si in the columns of Si 212 interact to convert received X-ray radiation into an electrical charge (signal, pulse, etc.) via electron-hole pair generation. This is further described in application serial number EP 14186022.1, entitled "Encapsulated materials in porous particles, and filed on Sep. 23, 2014, the entirety of which is incorporated herein by reference. QD's in imaging detectors are also described in application publication number WO 2017/025888 A1, entitled "Quantum Dot Based Imaging Detector," and filed on Aug. 8, 2016, the entirety of which is incorporated herein by reference. Suitable QD's include lead sulfide (PbS) QD's and/or other QD's.

The pSi membrane 116 is electrically coupled to the metal pad 120 through the electrically conductive connection 202. This coupling electrically couples the Si in the columns of Si 212 and not the QD's 118 in the columnar holes 214 to the metal pad 120, as the QD's 118 in the columnar holes 214 are electrically insulated via the air or the insulation material in the recess 220 from the electrically conductive connection 202. The metal pad 120 is disposed on the substrate 122. The electrical signal is routed from the pSi membrane 116 through the electrically conductive connection 202 and the metal pad 120 to the substrate 122, where it is readout through the one or more vias 206 and the one or more pads 204.

A size of a pixel is determined by a surface area of the metal pad 120. For example, the size of the pixel in the illustrated embodiment is determined by the number of columns of Si 212 in electrical contact with the metal pad 120. A smaller pixel requires the metal pad 120 to have a smaller surface area, which electrically contacts fewer of the columns of Si 212. A larger pixel requires the metal pad 120 to have a larger surface area, which electrically contacts more of the columns of Si 212. Generally, the pitch of the columnar holes 214 is on the order of microns, and a typical pixel size is on the order of hundreds of microns.

The top contact 115, the pSi membrane 116, and the substrate 122 extend out past the pixel area, i.e. out past the metal pad 120 and the electrically conductive connection 202. In this example, portions of a metal pad 120' and an electrically conductive connection 202' of a second pixel are shown to the left and portions of a metal pad 120" and an electrically conductive connection 202" of a third pixel are shown to the right of the pixel defined by the metal pad 120 and the electrically conductive connection 202. Gaps 226 electrically insulate neighboring pixels. The gaps 226 can be filled with air, an insulator, etc. In a variation, the pixel is an end pixel and does not have a neighboring pixel on each side.

Figure 4:
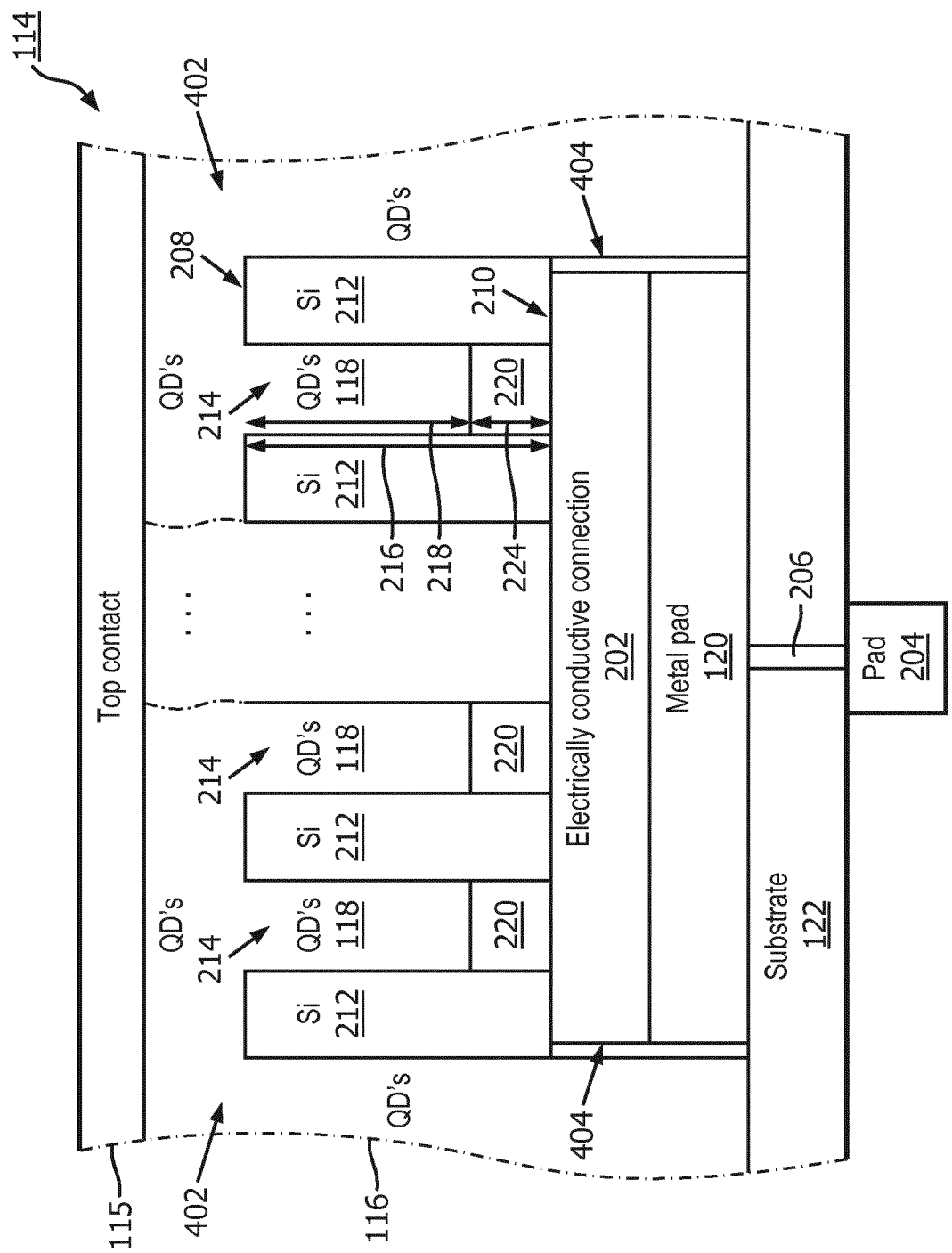
FIG. 4 schematically illustrates a variation of the example of the portion of the module of the QD-pSi radiation detector of FIG. 3.

FIG. 4 illustrates a variation of the module 114 shown in FIGS. 2 and 3. In this variation, the pSi membrane 116 further includes outer columns of QD's 402, which extend from the first side 208 of the pSi membrane 116 to the second side 210 and the substrate 122. Gaps 404 electrically insulate the metal pad 120 and the electrically conductive connection 202 from the outer columns of QD's 402. The gaps 404 can be filled with air, an insulator, etc. In one instance, the columns 402 provide direct electrical connections from the first side 208 of the pSi membrane 116 to the substrate 122.

An example of an electrical connection through a column of QD's is described in application Ser. No. 62/412,876, filed Oct. 27, 2017, and entitled "Radiation Detector Scintillator with an Integral Through-Hole Interconnect," which is incorporated by reference herein in its entirety. Alternatively, through-silicon vias (TSVs) and/or other approaches can be used for direct electrical connections between the first side 208 of the pSi membrane 116 and the substrate 122, where it is connected to the one or more pads 204 by the one or more vias 206.

Figure 5:
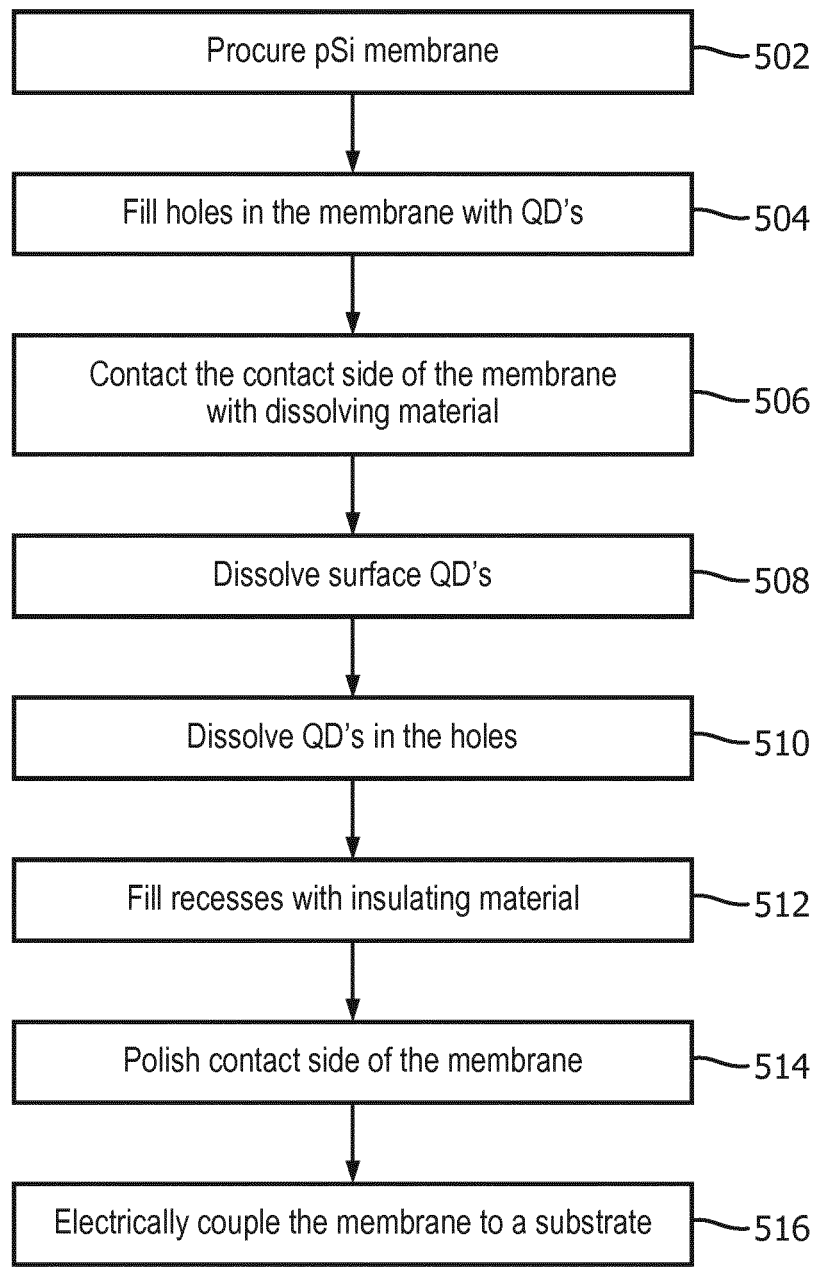
FIG. 5 illustrates an example method in accordance with an embodiment(s) herein.

FIG. 5 illustrates an example method in accordance with an embodiment(s) herein.

At 502, a pSi membrane with columnar holes entirely through the Si is procured.

At 504, the columnar holes are entirely filled with the QD's.

At 506, a contact side of the pSi membrane is placed in contact with (e.g., floated on) a viscous hydrocarbon capable of dissolving the QDs.

At 508, the viscous hydrocarbon dissolves surface ligand-capped PbS QDs.

At 510, the viscous hydrocarbon penetrates into the columnar holes, dissolving QDs therein and creating a recess therein. The depth of the penetration is determined based on the viscosity of the hydrocarbon and a contact time between the contact side and the viscous hydrocarbon. For example, the longer the contact time and/or the greater the viscosity, the greater the penetration depth. Generally, the contact time is a predetermined period of time t.

At 512, the recesses are filled with an insulating material via standard deposition process. Alternatively, the recesses are left empty.

At 514, the contact side of the pSi membrane is polished to remove material bound to the surface.

At 516, the contact side of the pSi membrane is electrically coupled to the substrate via an electrically conductive adhesive and a metal pad.

In the non-limiting example method described in connection with FIG. 5, any solution processed solid deposition method can be used to fill pores with active material. In a variation, a vapor/gas phase deposition (e.g., Atomic Layer Deposition, ALD) is used. Other approaches are also contemplated herein.

Figure 6:
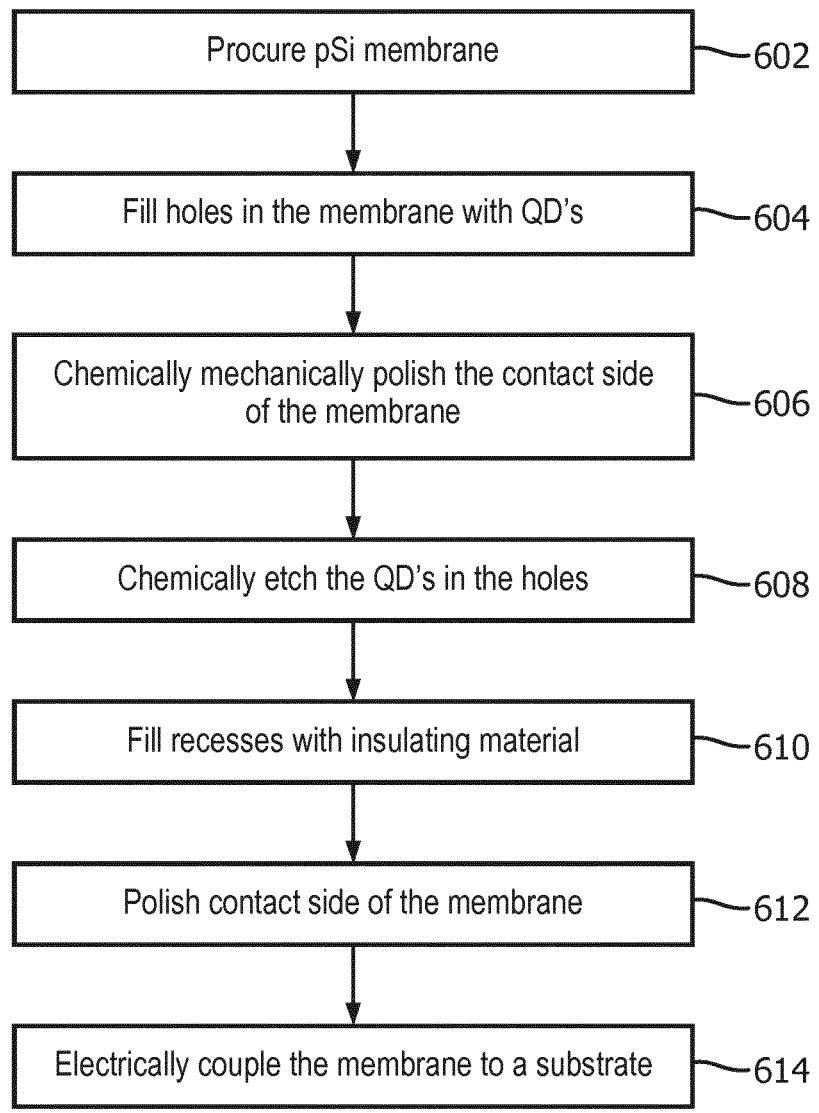
FIG. 6 illustrates another example method in accordance with an embodiment(s) herein.

FIG. 6 illustrates an example method in accordance with an embodiment(s) herein.

At 602, a pSi membrane with columnar holes entirely through the Si is procured.

At 604, the columnar holes are entirely filled with the QD's.

At 606, a contact side of the pSi membrane is chemically mechanically polished with a non-polar hydrocarbon-based polishing compound that mechanically and chemically removes surface QDs.

At 608, the exposed ends of the columnar holes are chemically etched to remove QD's in the columnar holes and create recesses.

At 610, the recesses are filled with an insulating material via standard deposition process. Alternatively, the recesses are left empty.

At 612, the contact side of the pSi membrane is polished to remove material bound to the surface.

At 614, the contact side of the pSi membrane is electrically coupled to the substrate via an electrically conductive adhesive and a metal pad.

In the non-limiting example method described in connection with FIG. 6, a non-polar solvent is used to mechanically and chemically remove surface QDs. In general, any solvent capable of re-solubilizing the deposited material without impacting the pSi can be used. Depending on the processing of the QDs or the chemical nature of the solid deposited in the pores, these may be polar (water, alcohol, etc.) or non-polar (hexane, toluene) or chemically reducing/oxidizing.

In another embodiment, a combination of a solvent treatment and chemical mechanical processing are employed to simultaneously abrade the back surface of the pSi membrane.

Figure 7:
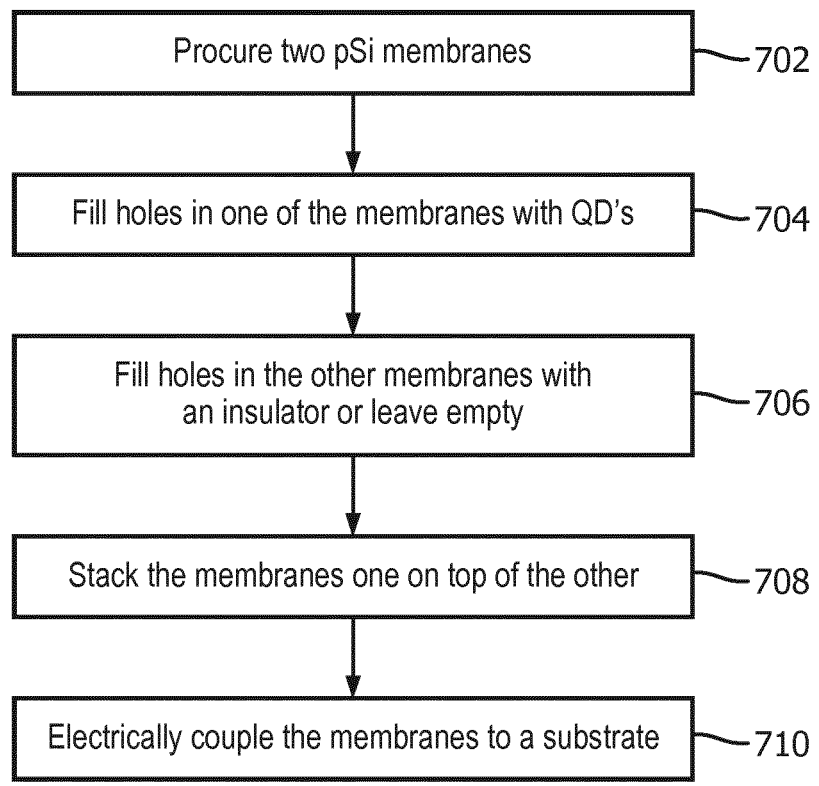
FIG. 7 illustrates yet another example method in accordance with an embodiment(s) herein.

FIG. 7 illustrates an example method in accordance with an embodiment(s) herein.

At 702, at least two pSi membranes are procured.

At 704, columnar holes of one of the pSi membranes are filled with the QD's.

At 706, columnar holes of the other of the pSi membranes are filled with an electrical insulator or left empty.

At 708, the two the pSi membranes are stacked with the pSi membrane with the QD's on top of the pSi membrane without the QD's.

At 710, the stacked pSi membranes are electrically coupled to a substrate via an electrically conductive adhesive and a metal pad.

It is to be understood that the above techniques allow proper pixel sizing and operation at this level to preserve both the increased efficiency and the lower cost of the detectors. Thus, once the assembly of the detector into a standard building block of a CT detector system is accomplished, imaging performance is improved in both conventional and spectral CT at a reduced cost. This applies to medical and baggage scanning multiple energy spectral X-ray radiation detectors, such a dual energy medical CT system, as well as phase contrast and dark field imaging applications where QD pSi radiation detectors have a columnar construction that can serve as a built-in grating between pixels, and/or other applications such as spectroscopy, etc.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An imaging module of an imaging system, comprising:
a porous silicon membrane including:
   a first side;
   a contact side opposite the first side;
   columns of silicon configured to extend from the first side to the contact side; and
   columnar holes interlaced with the columns of silicon and configured to extend from the first side to the contact side;
quantum dots in the columnar holes;
a metal pad electrically coupled to the columns of silicon of the porous silicon membrane, wherein the quantum dots in the columnar holes are electrically insulated from the metal pad; and
a substrate including an electrically conductive pad in electrical communication with the metal pad.

2. The imaging module of claim 1, further comprising:
a pixel, wherein the metal pad has a surface area, and a set of the columns of silicon in electrical communication with the surface area of the metal pad defines a size of the pixel.

3. The imaging module of claim 1, further comprising:
an electrically conductive connection disposed between the porous membrane and the metal pad.

4. The imaging module of claim 3, wherein the quantum dots in the columnar holes are electrically insulated from the electrically conductive connection.

5. The imaging module of claim 1, wherein the columnar holes include a recess between the quantum dots and the metal pad.

6. The imaging module of claim 5, wherein the recess is empty.

7. The imaging module of claim 5, wherein the recess includes an electrically insulating material.

8. The imaging module of claim 1, wherein the porous silicon membrane includes at least one column of silicon configured to extend from the first side to the substrate.

9. The imaging module of claim 1, further comprising:
a second porous silicon membrane with at least second columnar holes, wherein the second porous silicon membrane is disposed between the porous silicon membrane and the metal pad.

10. The imaging module of claim 1, wherein the porous silicon membrane further comprises a layer of quantum dots on the first side and a top contact disposed on the layer of quantum dots.

11. A computed tomography imaging system, comprising:
a radiation source configured to emit X-ray radiation;
a detector array configured to detect the X-ray radiation and generate an electrical signal indicative thereof, wherein the detector array includes a pixel, comprising:
   a first porous silicon membrane with first columns of silicon and first columnar holes with first quantum dots; and
   a first metal pad electrically coupled to the first columns of silicon and electrically insulated from the first quantum dots; and
a reconstructor configured to process the electrical signal and reconstruct volumetric image data.

12. The imaging system of claim 11, wherein the first columnar holes include a recess between the first quantum dots and the first metal pad, and the recess electrically insulates the first quantum dots and the first metal pad.

13. The imaging system of claim 11, wherein the first columnar holes include a recess between the first quantum dots and the first metal pad, and an insulation material in the recess is configured to electrically insulate the first quantum dots and the first metal pad.

14. The imaging system of claim 11, further comprising:
a first pixel, including the first metal pad and the first columns of silicon.

15. The imaging system of claim 14, further comprising:
a second pixel, including a second metal pad and second columns of silicon.

16. The imaging system of claim 11, further comprising another porous silicon membrane disposed between the first porous silicon membrane and the metal layer and configured to electrically insulate the first quantum dots and the first metal layer.

17. A method, comprising:
obtaining at least one porous silicon membrane having columns of silicon and columnar holes therethrough;
filling the columnar holes with quantum dots;
creating an insulator on a contact side of the porous silicon membrane for the quantum dots; and
electrically coupling only the columns of silicon to a substrate, wherein the quantum dots are electrically insulated from the substrate through the insulator.

18. The method of claim 17, wherein the insulator is air.

19. The method of claim 17, wherein the insulator is an insulation material.

20. The method of claim 17, wherein the insulator is another porous silicon membrane.

* * * * *